United States Patent [19]

Haber et al.

[11] Patent Number: 4,790,827
[45] Date of Patent: Dec. 13, 1988

[54] SHIELDED SAFETY SYRINGE

[75] Inventors: Terry M. Haber, Lake Forest; Clark B. Foster, El Toro; William H. Smedley, Lake Elsinore, all of Calif.

[73] Assignee: Habley Medical Technology Corporation, Laguna Hills, Calif.

[21] Appl. No.: 118,767

[22] Filed: Nov. 9, 1987

Related U.S. Application Data

[63] Continuation-in-part of Ser. No. 043,042, Apr. 27, 1987, Pat. No. 4,758,231.

[51] Int. Cl.⁴ .............................................. A61M 5/32
[52] U.S. Cl. .................................... 604/198; 604/263; 128/763
[58] Field of Search ............... 604/198, 195, 194, 187, 604/196, 263; 128/763, 764, 765

[56] References Cited

U.S. PATENT DOCUMENTS 4,631,057 12/1986 Mitchell .............................. 604/198
4,655,751 4/1987 Harbaugh ............................ 604/198
4,681,567 7/1987 Masters et al. ...................... 604/198

Primary Examiner—John D. Yasko
Attorney, Agent, or Firm—Morland C. Fischer

[57] ABSTRACT

A disposable syringe having particular application to vacuum tube phlebotomy and comprising respective inner and outer needle carrying and protective cylinders which are coaxially aligned and axially extensible relative to one another. The inner and outer cylinders may be locked in a retracted position, whereby a hypodermic needle is accessible for drawing blood samples from the patient to an evacuated tube at the inner cylinder. After the last blood sample has been taken, the inner and outer cylinders may be locked in an axially extended position, whereby the hypodermic needle is completely surrounded and shielded by the outer protective cylinder so as to permit the safe handling of the syringe while avoiding an accidental needle strike and the possible spread of a contagious disease.

20 Claims, 11 Drawing Sheets

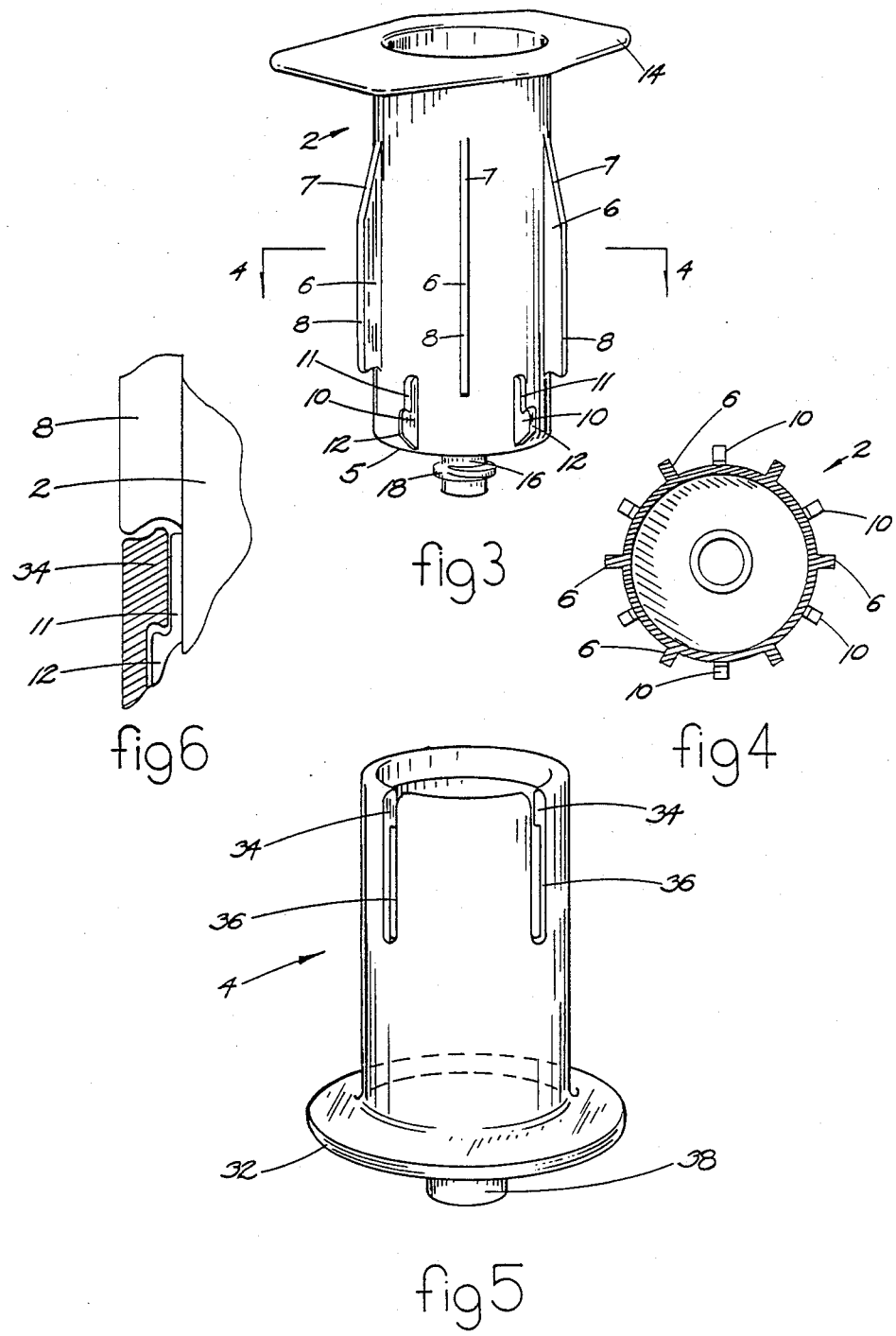

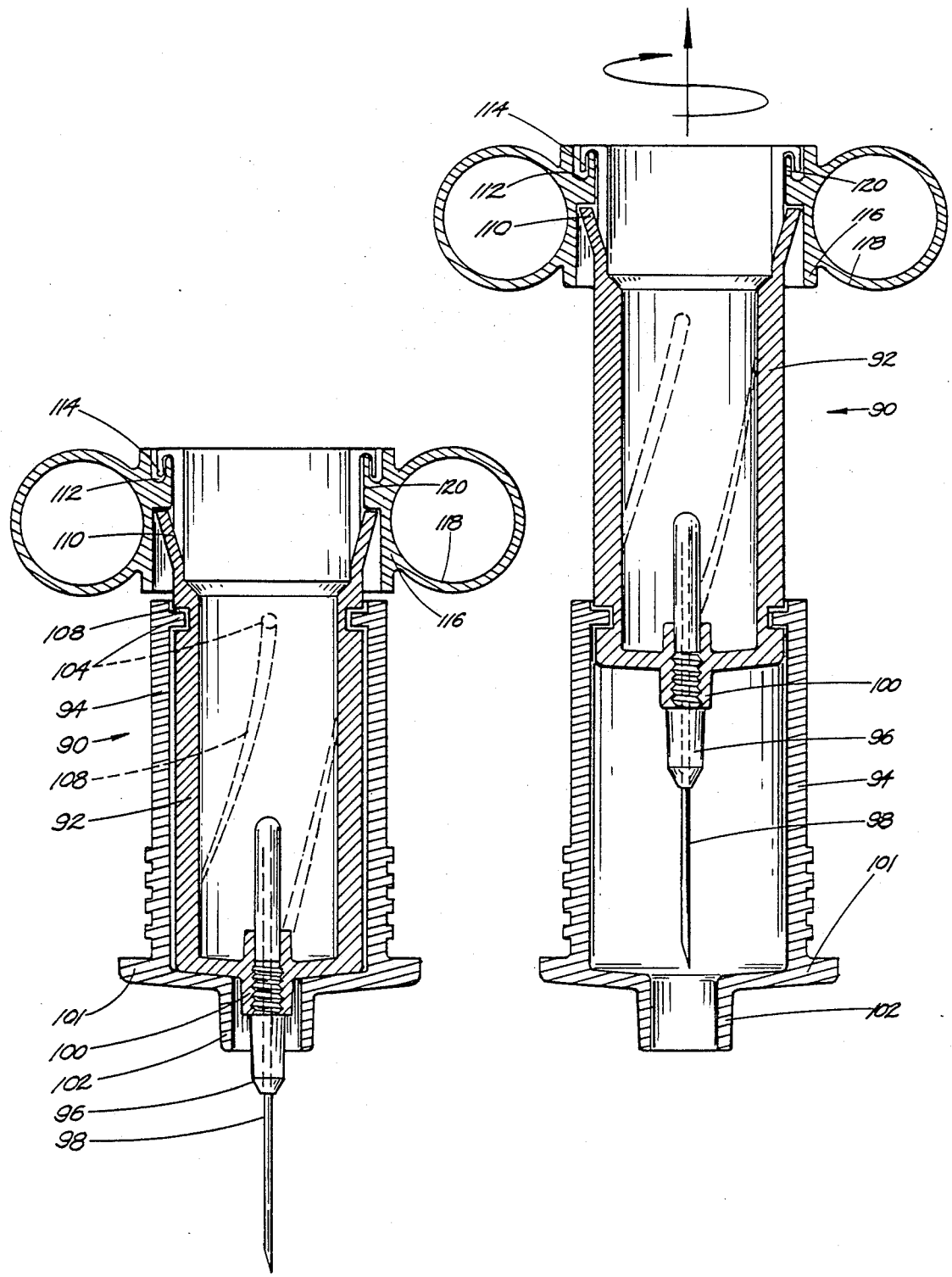

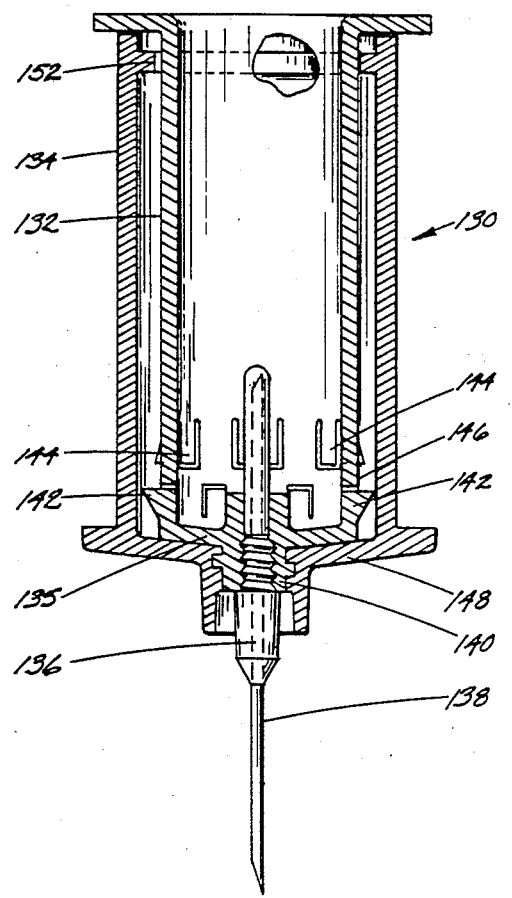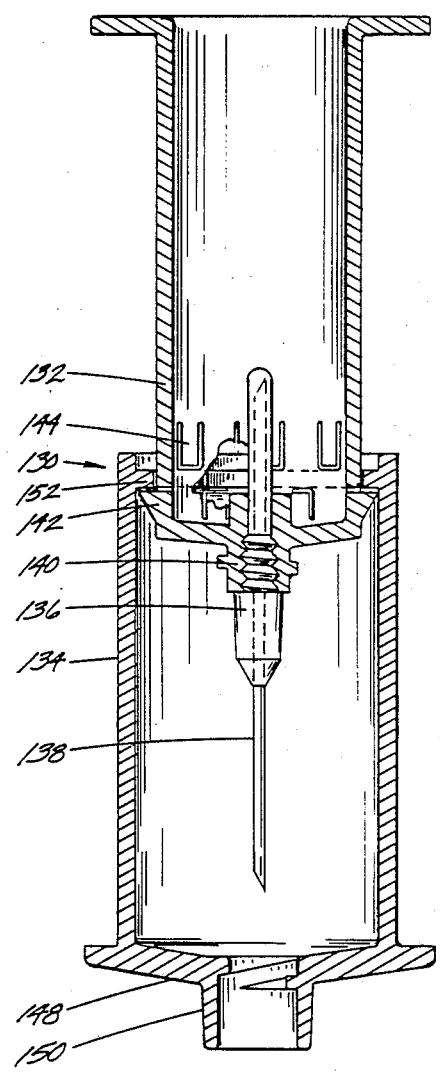
fig14
fig15

1

SHIELDED SAFETY SYRINGE

BACKGROUND OF THE INVENTION

CROSS-RELATED APPLICATIONS

This application is a continuation-in-part of patent application Ser. No. 43,042 filed Apr. 27, 1987 now U.S. Pat. No. 4,758,231.

FIELD OF THE INVENTION

This invention relates to a disposable syringe having particular application to vacuum tube phlebotomy and comprising means by which to shield an associated hypodermic needle to reduce the possibility of an accidental, and possibly life threatening, needle strike and the spread of contagious disease.

PRIOR ART

Hypodermic syringes are used for a variety of purposes. By way of a first example, the syringe may be used for vacuum tube phlebotomy, where samples of the patient's blood are successively drawn into respective evacuated tubes by way of a double ended hypodermic needle. In a second example, the syringe may be used to expulse fluid medication to a patient by way of a single ended hypodermic needle and a conventional injection procedure. In either example, the syring may be used to treat a patient having a communicable disease. Prior to disposal of the syringe, the hypodermic needle thereof is sometimes broken to prevent reuse. Health care workers are especially susceptible to accidental and potentially infectious needle strikes due to the careless handling or breaking of the needle and disposing of the syringe after use. The resulting mini-accidents caused by an accidental needle strike typically require a blood test for such diseases as AIDS and hepatitis. The corresponding cost and inefficiency of testing health care workers who have received an inadvertent needle strike result in considerable waste, which may be particularly damaging to a health care facility which is striving for economy.

The following U.S. Pat. Nos. provide examples of syringes having a hypodermic needle which may be shielded after use to prevent an accidental needle strike:

2,571,653 Oct. 16, 1951
4,356,822 Nov. 2, 1982
4,425,120 Jan. 10, 1984
4,631,057 Dec. 23, 1986

SUMMARY OF THE INVENTION

In general terms, a disposable syringe is disclosed having particular application to vacuum tube phlebotomy. The syringe comprises an inner hypodermic needle carrying syringe and an outer protective sleeve which are coaxially aligned and axially extensible relative to one another. That is, the inner cylinder and outer sleeve may be locked in a retracted position, whereby the needle is accessible for drawing blood from the patient to an evacuated phlebotomy tube at the inner cylinder. The inner cylinder and outer sleeve may also be locked in an axially extended position, whereby the needle is completely surrounded and shielded by the outer sleeve to assure safe handling of the syringe while avoiding an accidental needle strike and the possible spread of a contagious disease.

In a first embodiment of the invention, a plurality of longitudinally extending ribs and stops extend around the exterior of the inner cylinder. The stops are spaced distally from and interspersed between successive pairs of ribs. A lip is formed around the proximal end of the outer sleeve. The outer sleeve is advanced axially relative to the inner cylinder from the retracted to the extended position, such that the lip of the outer sleeve rides up and over the fins for receipt within the spaces between the ribs and stops. A self-locking feature is established when the lip of the outer cylinder is received between the ribs and stops of the inner cylinder to prevent the detachment of the outer sleeve from the inner cylinder and a return of the outer sleeve to the retracted position.

In a second embodiment, proximal and distal grooves are formed in and around the periphery of the inner cylinder. Each of a pair of spring-like locking members includes an oppositely extending arm and leg which are hingedly connected to a respective pivot at the proximal end of the outer sleeve. The inner cylinder and outer sleeve are locked in the retracted position when the legs of the locking members are received in the proximal groove of the inner cylinder. Equal and opposite compressive forces are applied to the arms of the locking members to cause the legs thereof to rotate out of the proximal groove in the inner cylinder. The outer sleeve is then axially advanced relative to the inner cylinder from the retracted to the extended position. A self-locking feature is established when the normal bias of the spring-like locking members automatically rotates the respective legs thereof into the distal groove of the inner cylinder to prevent the detachment of the outer sleeve from the inner cylinder.

In a third embodiment, a plurality of longitudinally aligned, spiraling grooves are formed in the inner cylinder. A corresponding plurality of raised bumps extend radially inward from the outer sleeve. The inner cylinder and outer sleeve are locked in the retracted position when the bumps of the outer sleeve are received at the proximal ends of respective grooves in the inner cylinder. The inner cylinder is axially advanced relative to the outer sleeve from the retracted to the extended position, such that the bumps of the outer sleeve ride through the spiraling grooves of the inner cylinder to cause the inner cylinder to rotate. A self-locking feature is established when the bumps of the outer sleeve are received at the distal ends of the spiraling grooves to prevent the detachment of the inner cylinder from the outer sleeve.

In a fourth embodiment, a first and second series of relatively short ramps extend outwardly from the periphery of the inner cylinder. A first of the series of ramps are spaced proximally from and interspersed between successive pairs of the second series of ramps. A rim extends inwardly from the proximal end of the outer sleeve. The outer sleeve is advanced axially relative to the inner cylinder from the retracted to the extended position, such that the rim of the outer sleeve rides up and across the first series of ramps for receipt within an annular gap established between the first and second series of ramps. A self-locking features is established when the rim of the outer cylinder is received within said gap to prevent the detachment of the outer sleeve from the inner cylinder and a return of the outer sleeve to the retracted position.

In a fifth embodiment, a first and second series of relatively short ramps project outwardly and in different directions from the respective intersections of adjacent sidewall which define a hexagonal inner cylinder.

A first of the series of ramps are spaced proximally from the second series of ramps. A rim extends inwardly from the proximal end of the outer sleeve. The outer sleeve is advanced axially relative to the inner cylinder from the retracted to the extended position, such that the rim of the outer sleeve rides up and across the first series of ramps for receipt within an annular gap established between the first and second series of ramps. A self-locking feature is established when the rim of the outer cylinder is received within said gap to prevent the detachment of the outer sleeve from the inner cylinder and a return of the outer sleeve to the retracted position.

In a sixth embodiment, a radially inward extending annular rim is formed around the proximal end of the outer sleeve. A flange extends radially outward from the proximal end of the inner cylinder. A recess or gap is established at the proximal end of the inner cylinder between the flange and an axially spaced, ramp-shaped catch. A recess or locking groove is established at the distal end of the inner cylinder between a pair of axially spaced, ramp-shaped lips which extend peripherally and continuously around said distal end. The annular rim of the outer sleeve is releasably received in the proximal gap of the inner cylinder to retain the inner cylinder and outer sleeve in a retracted position relative to one another. The annular rim of the outer sleeve may be released from the proximal groove of the inner cylinder, so that the sleeve can be advanced axially relative to the inner cylinder from the retracted to the extended position, such that the rim of the outer sleeve is received in the distal locking groove of said inner cylinder. A self-locking feature is established when the rim of the outer sleeve is received within the distal locking groove of said inner cylinder to prevent the detachment of the outer sleeve from the inner cylinder and a return of the outer sleeve to the retracted position.

BRIEF DESCRIPTION OF THE DRAWINGS

FIG. 3 is an isometric illustration of the inner cylinder;

FIG. 4 is a cross-section taken along lines 4—4 of FIG. 3;

FIG. 5 is an isometric illustration of the outer sleeve;

FIG. 6 is an enlarged detail taken from FIG. 2;

FIG. 10 shows a cross-section of the shielded syringe according to a third embodiment of the invention having an inner needle carrying cylinder and an outer protective sleeve locked in a retracted position relative to one another;

FIG. 11 shows the cross-section of the syringe of the third embodiment with the inner cylinder and outer sleeve axially advanced relative to one another to the extended position;

FIG. 14 shows a cross-section of the shielded syringe according to a fourth embodiment of the invention having an inner needle carrying cylinder and an outer protective sleeve locked in a retracted position relative to one another;

FIG. 15 shows the cross-section of the syringe of the fourth embodiment with the inner cylinder and outer sleeve axially advanced relative to one another to the extended position;

DESCRIPTION OF THE PREFERRED EMBODIMENT

Figures 1, 2:
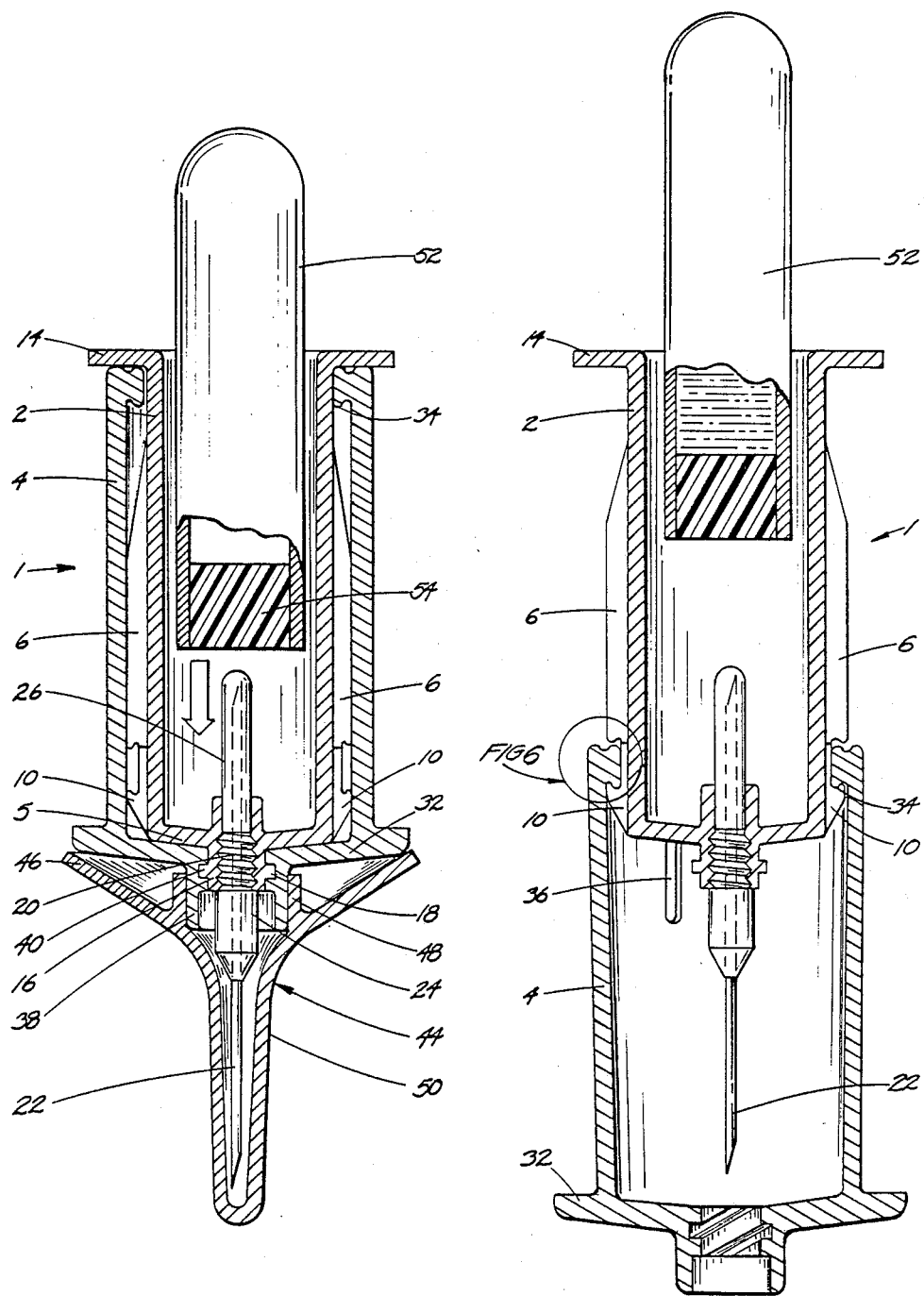
FIG. 1 shows a cross-section of a shielded syringe according to a first embodiment of the invention having an inner needle carrying cylinder and an outer protective sleeve locked in a retracted position relative to one another.
FIG. 2 shows the cross-section of the syringe with the inner cylinder and outer sleeve axially advanced relative to one another to the extended position.

A first embodiment of the present invention for a shielded safety syringe is best described while referring to FIGS. 1-6 the drawings. Although the syringes illustrated in the drawings hereof have particular application to vacuum tube phlebotomy (i.e. to successively drawing one or more samples of blood into respective vacuum tubes), it is to be expressly understood that the safety features of this invention are also applicable to a syringe in which a fluid medication is expulsed into a recipient by means of a conventional injection procedure. Referring initially to FIG. 1, there is shown a hypodermic syringe assembly 1 comprising an inner syringe barrel or cylider 2 and a cylindrical outer protective sleeve 4. The inner cylinder 2 and outer sleeve 4 are coaxially aligned and axially extensible relative to one another, such that the outer sleeve 4 is adapted for movement between a retracted position (of FIG. 1) and an axially extended position (of FIG. 2).

Details of the inner syringe cylinder 2 are disclosed while referring concurrently to FIGS. 1, 3 and 4 of the drawings. Inner cylinder 2 is preferably formed from a clear plastic material and has an open proximal end and a wall 5 which defines a substantially closed distal end. Coextensively formed with and projecting radially outward from the inner cylinder 2 are a series of elongated ribs 6. Ribs 6 extend longitudinally and in spaced, parallel alignment with one another around the exterior of inner cylinder 2. Each rib 6 includes a proximally oriented ramp portion 7 and a contiguous, distally oriented step portion 8 (best shown in FIG. 3).

Also coextensively formed with and projecting radially outward from the inner cylinder 2 are a series of relatively short fins 10. Fins 10 are arranged in spaced, parallel alignment with one another around the distal end of inner cylinder 2. However, and as is best shown in FIGS. 3 and 4 of the drawings, the fins 10 are interspersed between respective pairs of ribs 6. Each fin 10 includes a proximally oriented seat portion 11 and a contiguous, upwardly extending and distally oriented stop portion 12. As best shown in FIG. 3, the seat portions 11 of fins 10 lie below and between the step portions 8 of ribs 6 and the stop portions 12 of fins 10, for a purpose which will be described in greater detail hereinafter.

Extending around the open proximal end of inner cylinder 2 is a flange 14. Projecting outwardly from the distal end wall 5 of inner cylinder 2 is a neck 16. A screw thread 18 is formed around the outer periphery of neck 16 to be mated to a corresponding screw thread formed in the distal end of outer sleeve 4 in order to interconnect the distal ends of inner cylinder 2 and outer sleeve 4 when the outer sleeve is moved to a retracted position relative to the inner cylinder and a hypodermic needle 22 is to be made accessible.

A hole is formed through the neck 16 to define a distal bore which communicates with the interior of inner cylinder 2. The distal bore is threaded to receive therewithin a correspondingly threaded end 20 of a hub 24 which carries a conventional double ended needle 22. The needle carrying hub 24 is removably secured to the distal bore within neck 16, so that a first end of the needle 22 projects into the inner cylinder 2 and the opposite end thereof projects outwardly from the inner cylinder. A soft rubber sheath 26 covers the end of the needle 22 which projects into the inner cylinder 2.

Details of the outer protective sleeve 4 are now described while referring concurrently to FIGS. 1 and 6 of the drawings. Outer sleeve 4 is preferably formed from a resilient plastic material and has an open proximal end and a flanged wall 32 which defines a substantially closed distal end. An annular lip 34 extends around the interior of the open proximal end. A plurality of parallel aligned, longitudinally extending slots 36 (best shown in FIG. 6) are formed through outer sleeve 4 from the open proximal end thereof. The slots 36 maximize the flexibility of the proximal end of sleeve 4 when such end is snapped into locking engagement with the inner cylinder 2, in a manner that will soon be disclosed when referring to FIG. 2.

Projecting outwardly from the distal end wall 32 of outer sleeve 4 is a hollow neck 38. The neck 38 of outer sleeve 4 is sized to accommodate the neck 16 of inner cylinder 2 therewithin. A screw thread 40 is formed around the inside periphery of neck 38 to be mated, as previously indicated, to the corresponding screw thread 18 formed around the neck 16 (best illustrated in FIG. 1) when the outer sleeve 4 is located in the retracted position relative to inner cylinder 2 and the distal ends of inner cylinder 2 and outer sleeve 4 are interconnected at their respective necks 16 and 38 to permit access to needle 22.

A flared sheath 44 is also disclosed by which to avoid an accidental needle strike as a consequence of a careless handling of the syringe 1 with the needle 22 exposed. As is best shown in FIG. 1, the protective sheath 44 has a conical base 46 which is sized to surround the flanged distal end wall 32 of outer sleeve 4. An annular receptacle 48 extends from the conical base 46 for receiving therewithin the neck 38 of outer sleeve 4 in order to removably attach the sheath 44 to the outer sleeve (i.e. at the distal end of syringe 1). Coextensively formed with and projecting from the conical base 46 of sheath 44 is a tapered nose portion 50 in which the needle 22 is to be located. That is to say, the protective sheath 44 is attached to the distal end of syringe 1 when the outer sleeve 4 is located in the retracted position relative to inner cylinder 2, such that needle 22 is exposed. By virtue of the conical base 46 of flared sheath 44, a relatively large target area and guide are provided by which to reliably and automatically align the needle 22 for receipt within nose portion 50. In this fashion, the protective sheath 44 and the wide target area provided by the conical base 46 thereof advantageously enable the syringe user to accurately and safely locate a hypodermic needle within a shielded, protective housing while avoiding the possibility of inadvertently striking himself, a problem which is inherent with conventional narrow bodied needle caps.

The operation of the syringe 1 is best disclosed when referring concurrently to FIGS. 1-6 of the drawings. In FIG. 1, the outer sleeve 4 is located in the retracted position relative to inner cylinder 2, and the lip 34 of outer sleeve 4 is disposed proximally of the ribs 6 which extend along inner cylinder 2. The protective sheath 44 is then removed from the syringe 1 to make the exposed needle 22 accessible for penetrating the skin of the patient. A conventional, evacuated phlebotomy tube 52 having a rubber stopper 54 located in the open end thereof is moved through the open proximal end of inner cylinder 2. The tube 52 is then moved into contact with the needle 22 at the interior of cylinder 2, such that the needle penetrates the rubber stopper 54. A blood sample is automatically suctioned, in a well-known manner, from the patient to fill the tube 52 via needle 22.

When the last blood sample has been taken, the hypodermic needle 22 is withdrawn from the patient. In order to prevent an accidental needle strike and the possible spread of contagious disease from a contaminated needle, the previously connected distal ends of inner cylinder 2 and outer sleeve 4 are rotated out of engagement with one another, and the outer sleeve 4 is moved to an axially extended position relative to inner cylinder 2 (best represented in FIG. 2) by grasping the inner cylinder 2 at flange 14 and outer cylinder 4 below flanged end wall 32 and sliding the sleeve 4 over the cylinder 2. More particularly, the displacement of outer cylinder 4 causes a corresponding movement of the annular lip 34 up the ramps 7 and over the steps 8 of the ribs 6 (best shown in FIG. 3). Because of its resilient nature, the lip 34 (which is separated into flexible lip sections by the longitudinally extending slots 36) will be rotated outwardly and, thereby, stressed as the lip 34 rides up the ramp portions 7 of ribs 6. The continued axial advancement of outer sleeve 4 relative to inner cylinder 2 will cause the lip 34 to be snapped onto the recessed seats 11 of fins 10 between the stops 12 thereof and the steps 8 of fins 6 (best shown in FIG. 6).

Thus, a positive, self-locking feature is established, because the lip 34 of outer sleeve 4 is securely and permanently retained below and between the elevated steps 8 and stops 12, whereby to prevent both the continued axial advancement of outer sleeve 4 past inner cylinder 2 as well as a return of the outer sleeve to the retracted position. What is more, because the seats 11 of fins 10 extend above the exterior surface of inner cylinder 2, the lip 34 of outer sleeve 4 will not return to a totally relaxed condition, but will remain slightly stressed, when received upon the seats 11. The corresponding compressive force exerted by the flexible lip 34 of sleeve 4 will prevent the removal of lip 34 from the recessed seats 11 and the detachment of the outer sleeve 4 from the inner cylinder 2.

By virtue of the foregoing, a disposal cartridge (of FIG. 2) is created having the inner cylinder 2 and outer sleeve 4 locked in an axially extended position relative to one another with the hypodermic needle 2 surrounded, completely shielded, and rendered irretrievable therewithin so as to permit the safe handling of syringe 1 while avoiding an accidental needle strike. Accordingly, the specimen tube 52 may be detached from needle 22 and removed through the open proximal end of inner cylinder 2. However, because of the permanent nature of the interlocking engagement between inner cylinder 2 and outer sleeve 4, the syringe 1 cannot be reused. Moreover, the used syringe is in a condition to permit safe disposal without requiring the removal or handling of the needle 22 as has heretofor been necessitated as a consequence of many conventional syringe assemblies.

Figure 7:
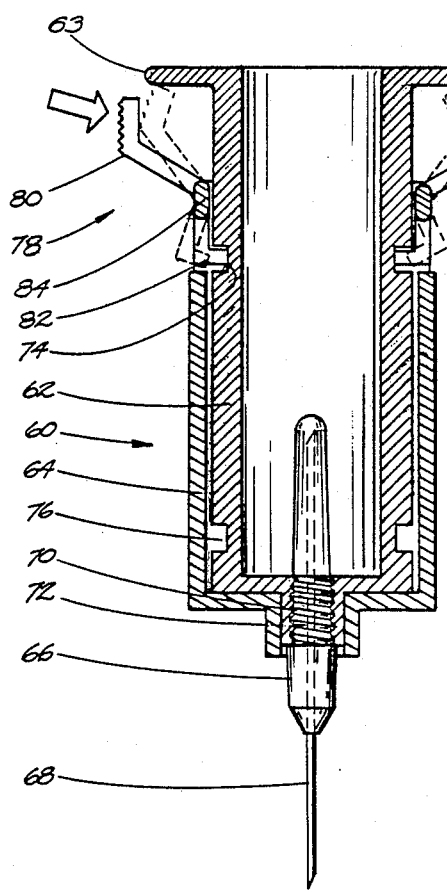
FIG. 7 shows a cross-section of a shielded syringe according to a second embodiment of the invention having an inner needle carrying cylinder and an outer protective sleeve locked in a retracted position relative to one another.
Figure 8:
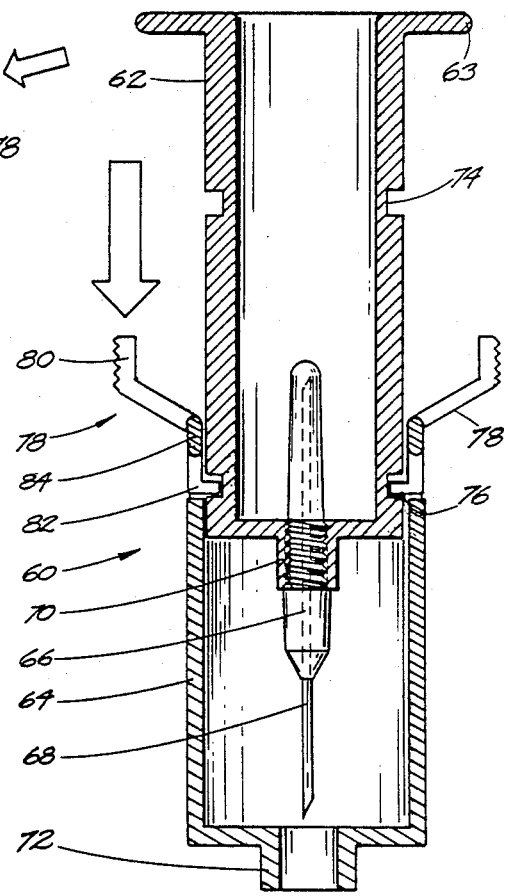
FIG. 8 shows a cross-section of the syringe of the second embodiment with the inner cylinder and outer sleeve axially advanced relative to one another to the extended position.
Figure 9:
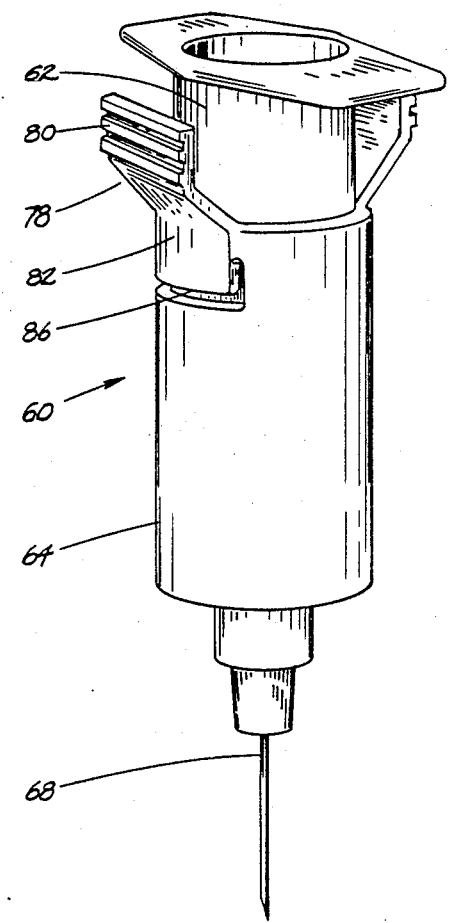
FIG. 9 is an isometric illustration of the syringe according to the second embodiment.

FIGS. 7-9 of the drawings show a second embodiment of the present invention for a shielded safety syringe. Like the syringe 1 of FIGS. 1-6, the syringe 60 of FIGS. 7-9 includes an inner syringe barrel or cylinder 62 and a cylindrical outer protective sleeve 64. The proximal ends of cylinder 62 and sleeve 64 are open, and the distal ends thereof are substantially closed. The inner cylinder 62 and outer sleeve 64 are coaxially aligned and axially extensible relative to one another, such that outer sleeve 64 is adapted for movement between a retracted position (of FIG. 7) to an axially extended position (of FIG. 8).

Also like the syringe 1, syringe 60 includes a screw threaded hub 66 which carries a double ended hypodermic needle 68. The needle carrying hub 68 is retained within a distal bore formed through a neck 70 which extends from the distal end wall of inner cylinder 62, whereby one end of needle 68 projects outwardly from the inner cylinder 62, and the opposite end projects into the cylinder 62 for communication with an evacuated phlebotomy tube (not shown). The outer sleeve 64 includes a hollow neck 72 which is sized to accommodate the neck 70 of inner cylinder 62 so that a tight friction fit is formed therebetween when the outer sleeve 64 is located at the retracted position relative to inner cylinder 62. Accordingly, the distal ends of inner cylinder 62 and outer cylinder 64 can be temporarily joined at their respective necks 70 and 72 to retain syringe 60 in the retracted position and thereby provide access to needle 68 (best shown in FIG. 7).

The inner cylinder 62 includes a pair of grooves 74 and 76 extending around the periphery thereof. A first groove 74 is located below the open proximal end of cylinder 62, and the second groove 76 is located above the distal end wall thereof.

The outer sleeve 64 includes a pair of oppositely disposed, spring-like locking members 78 by which to secure the outer protective sleeve 64 in either of the retracted or axially extended positions relative to inner cylinder 62. More particularly, each locking member 78 includes an arm 80 and a leg 82 which are coextensively formed with and hingedly connected to the outer sleeve 64 at a joint 84 located at the periphery of the open proximal end of sleeve 64. As will soon be explained, the arms and legs 80 and 82 of locking members 78 are adapted to rotate around their respective joints 84 to form what is known in the art as a living hinge assembly. To accommodate the rotation of the legs 82 of locking members 78 towards inner cylinder 62, laterally extending slots (best shown in FIG. 9) are formed through the outer sleeve 64 below the joints 84.

The operation of the syringe 60 is best described while continuing to refer to FIGS. 7-9 of the drawings. In FIG. 7, the outer sleeve 64 is located at the retracted position relative to inner cylinder 62 and the legs 82 of locking members 78 are shown in their normal bias extending through the slots 86 (of FIG. 3) in outer sleeve 64 for receipt by the proximal groove 74 of inner cylinder 62. With the legs 82 of locking members 78 located in grooves 74, the arms 80 are radially spaced from the outer sleeve 64. The hypodermic needle 68 is now exposed for penetrating the skin of the patient, so that a phlebotomy tube (not shown) may be infused with a sample of the patient's blood. After the last blood sample has been taken, and in order to avoid an accidental needle strike, the inner cylinder 62 is grasped, below major flange 63, and the outer sleeve 4 is moved to an axially extended position (of FIG. 8) relative to inner cylinder 62 by sliding the sleeve 64 thereover.

That is to say, equal and opposite compressive forces are applied (in the directions of the reference arrows of FIG. 7) to the outwardly extending arms 80 of locking members 78, whereby arms 80 are rotated around pivot 84 against the normal spring bias thereof to a new position (shown in phantom) in closer proximity to outer sleeve 64. The rotation of arms 80 causes a corresponding rotation of legs 82 in an opposite direction around pivot 84 and out of proximal groove 74 to a detached position (also shown in phantom) relative to the inner cylinder 62. Accordingly, outer sleeve 64 is free to slide over inner cylinder 62 in the direction indicated by the reference arrow of FIG. 8.

After outer sleeve 64 has been axially advanced, such that the proximal end thereof is moved adjacent the distal end of inner cylinder 62, the spring biased legs 82 of locking members 78 are automatically rotated around hinges 84, through the slots 86, and snapped into receipt by the distal grooves 76 of inner cylinder 62. With the legs 82 of locking members 78 received within grooves 76, a positive, self-locking feature is established, whereby to prevent both the continued axial advancement and possible detachment of outer sleeve 64 from inner sleeve 62 as well as an inadvertent return of the outer sleeve 64 to the retracted position of FIG. 7. Therefore, a disposal cartridge is created (in FIG. 8) having the inner cylinder 62 and outer sleeve 64 locked and axially extended relative to one another with the hypodermic needle 68 completely surrounded and shielded, so as to permit the safe handling of the syringe 60 while avoiding an accidental needle strike and the possible spread of a contagious disease.

FIGS. 10-13 of the drawings show a third embodiment of the present invention for a shielded safety syringe. Like the syringes of FIGS. 1-9, the syringe 90 of FIGS. 10-13 includes an inner cylinder 92 and an outer protective sleeve 94 which are coaxially aligned and axially extensible relative to one another between a retracted position (of FIG. 10) and an axially extended position (of FIG. 11). The inner cylinder 92 has an open proximal end for receiving an evacuated phlebotomy tube (not shown) and a substantially closed distally end wall. A screw threaded hub 96, which carries a double ended needle 98, is retained within a distal bore formed through a neck 100 which extends from the distal end wall of inner cylinder 92, whereby one end of the needle 98 projects outwardly from the inner cylinder 92, and the opposite end projects into the cylinder 92 for communication with the phlebotomy tube.

The outer sleeve 94 includes an open proximal end for passing the inner cylinder 92 therethrough and a substantially closed, flanged distal end wall 101 having a hollow neck 102 extending outwardly therefrom. Neck 102 is sized to accommodate the neck 100 of inner cylinder 92, so that a tight friction fit is formed therebetween when the outer sleeve 94 is moved to a retracted position relative to inner cylinder 92. Accordingly, the distal ends of inner cylinder 92 and outer sleeve 94 can be temporarily joined at their respective necks 100 and 102 to retain syringe 90 in the retracted position and thereby permit access to the needle 98 (best shown in FIG. 10). A plurality (e.g. three) of raised locking bumps 104 are coextensively formed with and project radially inward from the outer sleeve 94. The bumps 104 are spaced around the interior of outer sleeve 94 below the open proximal end thereof. A corresponding plurality (e.g. three) of parallel aligned, longitudinally extending slots 106 (best shown in FIG. 13) are respectively formed through outer sleeve 94 between pairs of bumps 104. The slots maximize the flexibility of outer sleeve 94 for retaining the locking bumps 104 in engagement with the inner cylinder 92, as will soon be explained.

Figure 12:
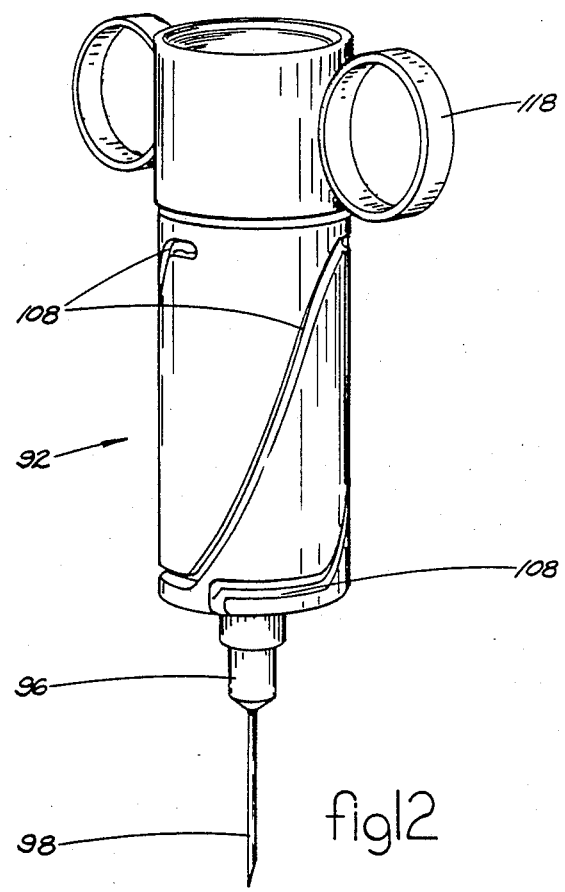
FIG. 12 is an isometric illustration of the inner cylinder of the syringe of the third embodiment.
Figure 13:
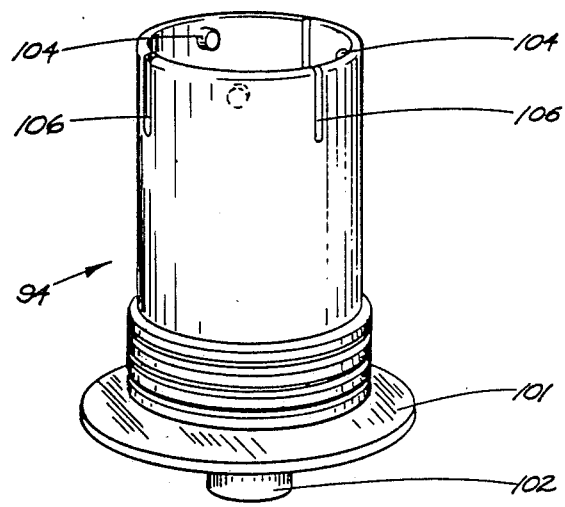
FIG. 13 is an isometric illustration of the outer sleeve of the syringe of the third embodiment.

As is best shown in FIG. 12, a series (e.g. three) of generally "S" shaped, longitudinally extending and spiraling grooves 108 are formed in the exterior of outer sleeve 94. Although an S-shaped groove is illustrated, it is to be expressly understood that grooves 108 may have any other suitable shape. The grooves 108 are spaced from one another around the periphery of outer sleeve 104 and provide guide paths through which the locking bumps 104 of inner cylinder 92 are adapted to ride when the inner cylinder 92 is moved axially between the retracted and extended positions relative to outer sleeve 94.

As is best shown in FIGS. 9 and 10, the open proximal end of inner cylinder 92 terminates at a flared portion 110. Flared portion 110 includes a slotted opening 112 extending therearound. A lip 114 is formed at the most distal aspect of flared portion 110. A cylindrical collar 116 having a pair of oppositely disposed, outwardly extending finger loop 118 and a coextensively formed, inwardly extending flange 120 is attached to the flared proximal portion 110 of inner cylinder 92. In the assembled syringe relationship shown in FIGS. 9 and 10, the flange 120 of collar 116 is received through the opening 112 in flared portion 110 and retained behind the lip 114. The lip 114 prevents the withdrawal of the flange 120 from opening 112 and the removal of collar 116 from the flared proximal portion 110 of inner cylinder 92. However, the inner cylinder 92 is free to rotate relative to both outer sleeve 94 and collar 116.

The operation of the syringe 90 is best described while continuing to refer to FIGS. 10-13. In FIG. 10, the inner cylinder 92 is located at the retracted position relative to outer sleeve 94 and the locking bumps 104 of inner cylinder 92 are positioned at the proximal ends of grooves 108. The hypodermic needle 98 is now exposed for penetrating the skin of the patient, so that a phlebotomy tube (not shown) may be infused with a sample of the patient's blood. After the last blood sample has been taken, and in order to avoid an accidental needle strike, the outer sleeve 94, below flanged end wall 101, and the finger loops 118 of the collar 116 are grasped, and the inner cylinder 92 is pulled to the axially extended position (of FIG. 11) relative to outer sleeve 94, whereby cylinder 92 is caused to simultaneously slide and rotate through sleeve 94. That is to say, the bumps 104 of outer sleeve 94 ride along the spiraling grooves 108 from the proximal to the distal ends thereof until inner cylinder 92 has been axially advanced, such that the distal end thereof is moved adjacent the proximal end of outer sleeve 94. The axial advancement of inner cylinder 92 through outer sleeve 94 and the corresponding travel of locking bumps 104 through spiraling grooves 108 causes an automatic rotation of the inner cylinder 92 relative to outer sleeve 94 and collar 116. The axial and rotational movement of inner cylinder 92, as the cylinder is moved through outer sleeve 94 to the axially extended position, is indicated by the pair of reference arrows in FIG. 11.

When the locking bumps 104 are seated at the distal ends of spiraling grooves 108, a self-locking feature is established, whereby to prevent both the continued axial advancement and possible detachment of inner cylinder 92 from outer sleeve 94 as well as an inadvertent return of inner cylinder 92 to the retracted position of FIG. 10. Therefore, a disposal cartridge is created (in FIG. 11) having the inner cylinder 92 and outer sleeve 94 axially extended and locked relative to one another with hypodermic needle 98 completely surrounded and shielded, so as to permit the safe handling of syringe 90 while avoiding an accidental needle strike and the possible spread of a contagious disease.

FIGS. 14-18 of the drawings show a fourth embodiment of the present invention for a shielded safety syringe. Like the previously described syringes of FIGS. 1-13, the syringe 130 of FIGS. 14-18 includes an inner cylinder 132 and an outer protective sleeve 134 which are coaxially aligned and axially extensible relative to one another from a retracted position (of FIG. 14) to an axially extended position (of FIG. 15). The inner cylinder 132 has an open, flanged proximal end for receiving an evacuated phlebotomy tube (not shown) and a substantially closed distal end wall 135. A screw threaded hub 136, which carries a double ended needle 138, is retained within a distal bore formed through a neck 140 which extends from the distal end wall 135 of inner cylinder 132, whereby one end of needle 138 projects outwardly from the inner cylinder 132, and the opposite end of needle 138 projects into the cylinder 132 for communication with the phlebotomy tube.

Figure 16:
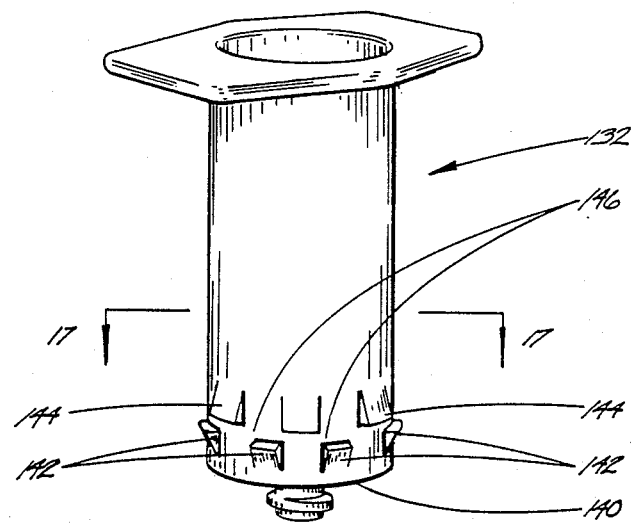
FIG. 16 is an isometric illustration of the inner cylinder of the syringe of the fourth embodiment.
Figure 17:
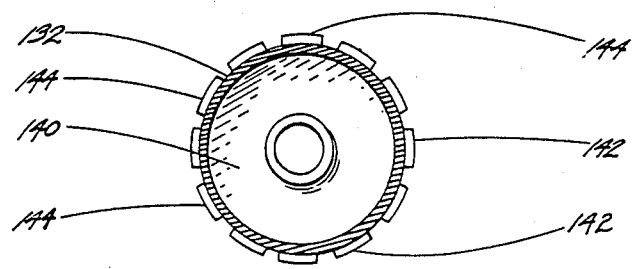
FIG. 17 is a cross-section taken along lines 17—17 of FIG. 16.
Figure 18:
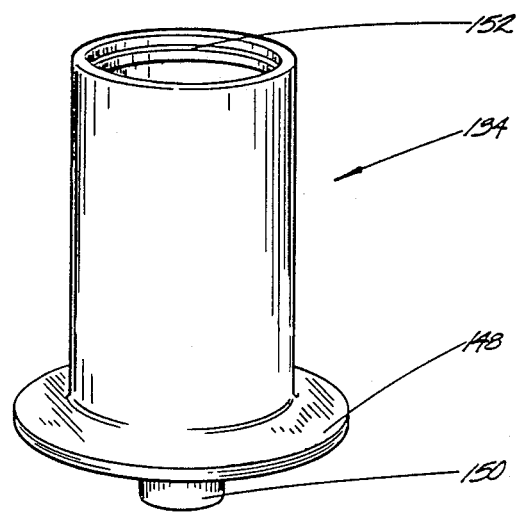
FIG. 18 is an isometric illustration of the outer sleeve of the syringe of the fourth embodiment.

Coextensively formed with and projecting outwardly from the inner cylinder 132 are first and second series of relatively short ramps 142 and 144 (best shown in FIGS. 16 and 17). A first of a series of ramps 142 extend in spaced, parallel alignment with one another around the distal end of inner cylinder 132. The second series of ramps 144 are spaced proximally from ramps 142 and also extend in spaced, parallel alignment with one another around inner cylinder 132. However, ramps 142 are interspersed between respective pairs of ramps 144. Ramps 142 slope upwardly in a proximally oriented direction, and ramps 144 slope upwardly in a distally oriented direction, such that the most elevated ends of ramps 142 and 144 oppose one another to establish a narrow, annular gap 146 in the space therebetween.

The outer sleeve 134 includes an open proximal end for passing the inner cylinder 132 therethrough and a substantially closed, flanged distal end wall 148 having a hollow neck 150 extending outwardly therefrom. The neck 150 of outer sleeve 134 is sized to accommodate the neck 140 of inner cylinder 132 therewithin. A screw thread is formed around the inside of the neck 150 of outer sleeve 134 to be mated to a corresponding screw thread formed around the neck 140 of inner cylinder 132 (best illustrated in FIG. 14). Accordingly, when the outer sleeve 134 is located in the retracted position relative to inner sleeve 132, the inner cylinder and outer sleeve may be interconnected to one another at their respective necks 140 and 150 to permit access to needle 138. An annular rim 152 (best shown in FIG. 18) is coextensively formed with and extends around the interior of outer sleeve 134 at the proximal end thereof for a purpose which will now be described.

The operation of the syringe 130 is now disclosed while continuing to refer to FIGS. 14-18 of the drawings. In FIG. 14, the outer sleeve 134 is located in the retracted position relative to inner cylinder 132, such that the annular rim 152 of outer sleeve 134 is positioned proximally from and out of engagement with the ramps 142 and 144 of the inner cyliner 132. The inner cylinder and outer sleeve are connected together at their respective screw threaded necks 140 and 150, whereby to expose the hypodermic needle 138 for penetrating the skin of a patient, so that a phlebotomy tube (not shown) may be infused with a sample of the patient's blood. After the last blood sample has been taken, and in order to avoid an accidental needle strike, the outer sleeve 134 is grasped, below flanged end wall 148, and pulled to the axially extended position (of FIG. 15) relative to inner cylinder 132.

The axial advancement of outer sleeve 134 causes a corresponding advancement of the rim 152, such that rim 152 travels up and across the proximally oriented series of ramps 144. The continued axial advancement of outer sleeve 134 relative to inner cylinder 132 will cause rim 152 to be snapped into the gap 146 between ramps 142 and 144. A positive self-locking feature is thereby established, because the rim 152 of outer sleeve 134 is securely and permanently retained within the gap 146 between the most elevated portions of ramps 142 and 144. Hence, the ramps 142 and 144 form stops to prevent both the continued axial advancement and possible detachment of the outer sleeve 134 from the inner cylinder 132 as well as an inadvertent return of the outer sleeve 134 to the retracted position of FIG. 14. Therefore, a disposal cartridge is created (in FIG. 15) having the inner cylinder 132 and outer sleeve 134 locked in the axially extended position with the hypodermic needle 138 completely surrounded and shielded, so that the syringe 130 may be safely handled while avoiding an accidental needle strike and the possible spread of a contagious disease.

Figure 21:
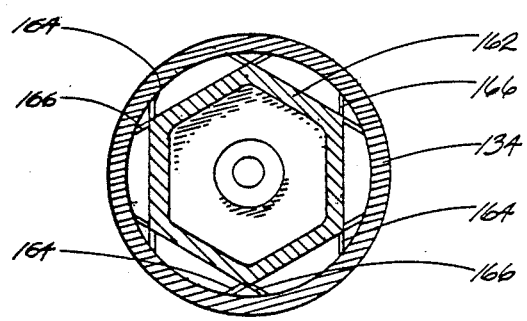
FIG. 21 is a cross-section taken along lines 21—21 of FIG. 19.
Figure 22:
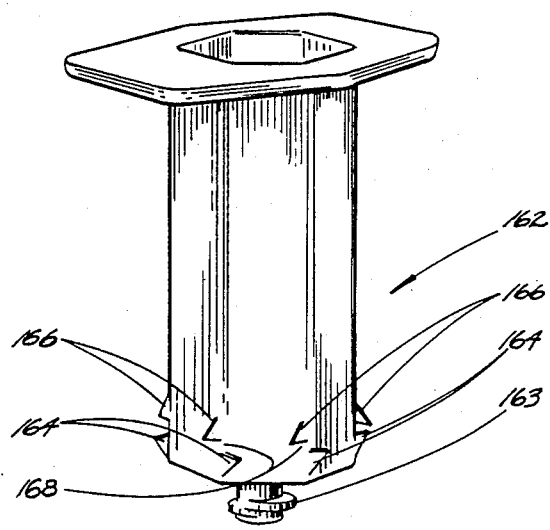
FIG. 22 is an isometric illustration of the inner cylinder of the syringe of the fifth embodiment.
Figure 23:
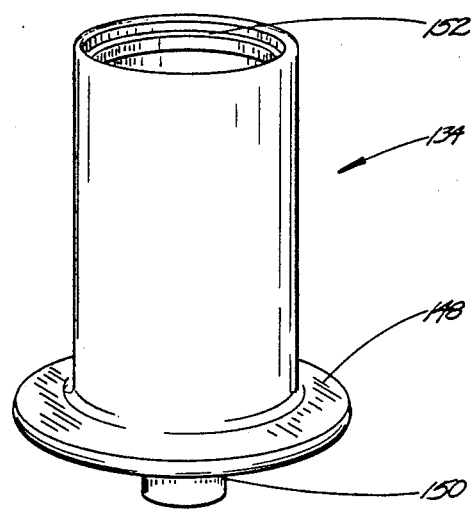
FIG. 23 is an isometric illustration of the outer sleeve of the syringe of the fifth embodiment.
Figure 24:
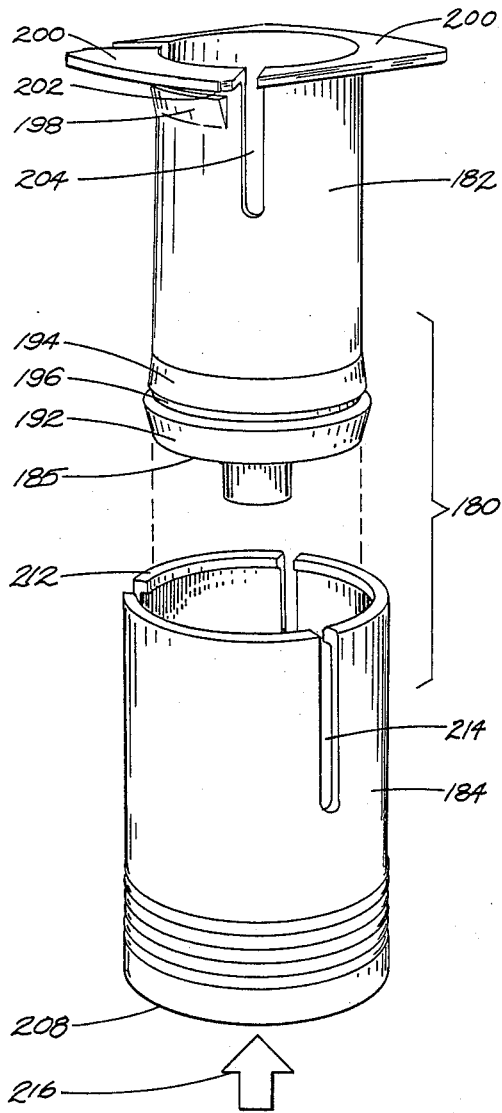
FIG. 24 is an isometric illustration of the shielded syringe according to a sixth embodiment of the invention having an inner needle carrying cylinder aligned for receipt by an outer protective sleeve.
Figure 27:
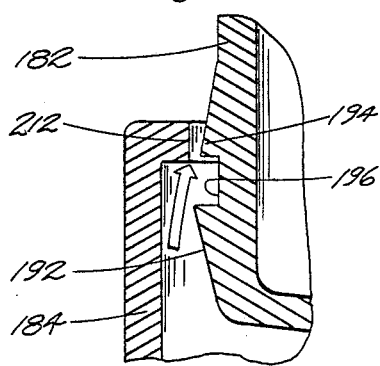
FIG. 27 shows an enlarged detail taken from FIG. 26.

FIGS. 19-23 of the drawings show a fifth embodiment of the present invention for a safety syringe. The syringe 160 of FIGS. 19-23 includes an inner cylinder and outer protective sleeve which are coaxially aligned and axially extensible relative to one another from a retracted position (of FIG. 19) to an axially extended position (of FIG. 20). As is best illustrated in FIG. 23, the outer sleeve 134 of syringe 160 is identical to the outer sleeve which was previously described when referring to the syringe 130 of FIGS. 14-18. Therefore, identical reference numerals will be used to describe the outer sleeve 134 of FIGS. 19-23, and the details thereof will be omitted. Likewise, the screw threaded hub 136 and hypodermic needle 138 of syringe 160 are identical to those of the syringe 130. Therefore, identical reference numerals will also be used to refer to hub 136 and needle 138.

As is best shown in FIG. 21, the inner cylinder 162 of the syringe 160 has a hexagonal cross-section comprising a plurality of contiguous sidewalls. Inner cylinder 162 also has an open flanged proximal end for receiving an evacuated phlebotomy tube (not shown) and a substantially closed distal end wall. The hypodermic needle carrying hub 136 is retained within a distal bore formed through a neck 163 which extends from the distal end wall of inner cylinder 162, whereby one end of needle 138 projects outwardly from the inner cylinder, and the opposite end of needle 138 projects into the cylinder for communication with the phlebotomy tube.

Coextensively formed with and projecting outwardly from the distal end of inner cylinder 162 are first and second series of short ramps 164 and 166 (best illustrated in FIG. 22). The first series of ramps 164 project outwardly in a first direction from the respective intersections of adjacent sidewalls which define hexagonal inner cylinder 162. A second series of ramps 166 are spaced proximally from ramps 164 and project outwardly in a second direction from the respective intersections of the sidewalls of inner cylinder 162. As is best shown in FIG. 21, an angle of approximately 120 degrees is formed between the first and second directions in which the first and second series of ramps 164 and 166 respectively extend from the intersections of the sidewalls of inner cylinder 162. Ramps 164 slope upwardly in a proximally oriented direction, and ramps 166 slope upwardly in a distally oriented direction, such that the most elevated ends 164 and 166 oppose one another to establish a narrow, annular gap 168 in the space therebetween.

Figure 19:
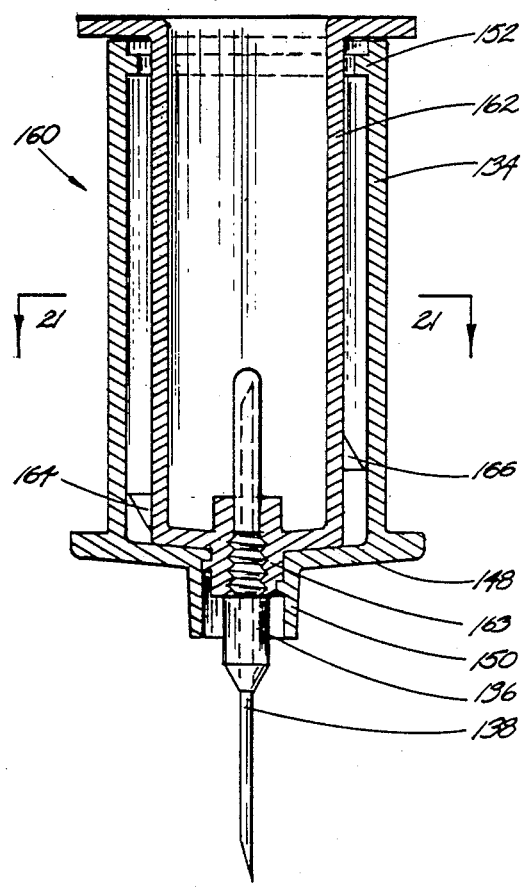
FIG. 19 shows a cross-section of the shielded syringe according to a fifth embodiment of the invention having an inner needle carrying cylinder and an outer protective sleeve locked in a retracted position relative to one another.
Figure 20:
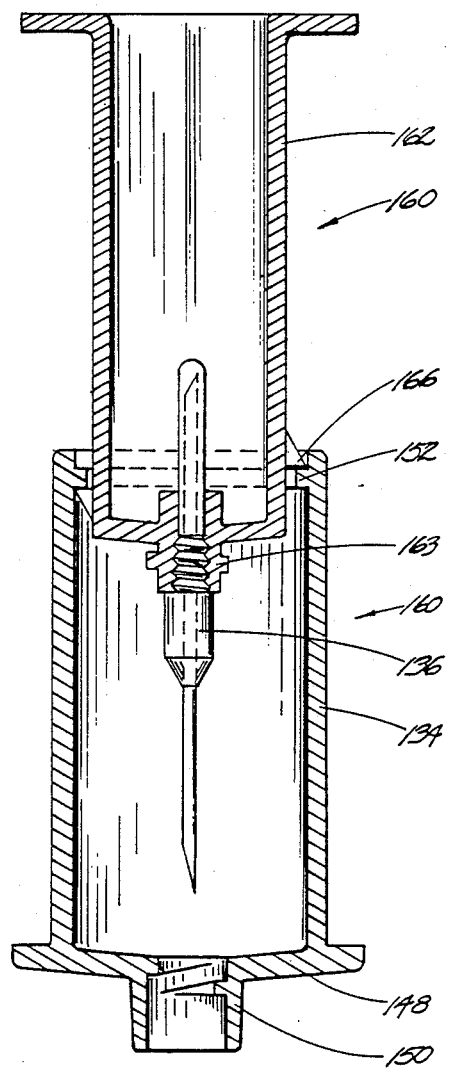
FIG. 20 shows the cross-section of the syringe of the fifth embodiment with the inner cylinder and outer sleeve axially advanced relative to one another to the extended position.

The operation of the syringe 160 is now described while continuing to refer to FIGS. 19-23 of the drawings. In FIG. 19, the outer sleeve 134 is located in the retracted position relative to inner sleeve 162, such that the annular rim 152 of outer sleeve 134 is positioned proximally from and out of engagement with the ramps 164 and 166 of the inner cylinder 162. The inner cylinder and outer sleeve are connected together at their respective screw threaded necks 163 and 150, whereby to expose the hypodermic needle 138 for penetrating the skin of a patient so that a phlebotomy tube (not shown) may be infused with a sample of the patient's blood. After the last blood sample has been taken, and in order to avoid an accidental needle strike, the outer sleeve 134 is grasped, below flanged end wall 148, and pulled to the axially extended position (of FIG. 20) relative to inner cylinder 162.

The axial advancement of outer sleeve 134 causes a corresponding advancement of the rim 152, such that rim 152 travels up and over the proximally oriented series of ramps 166. The continued axial advancement of outer sleeve 134 relative to inner cylinder 162 will cause rim 152 to be snapped into the gap 168 between ramps 164 and 166. A positive self-locking feature is thereby established, because the rim 152 of outer sleeve 134 is securely and permanently retained within the gap 168 between the most elevated portions of ramps 164 and 166. Hence, the ramps 164 and 166 form stops to prevent both the continued axial advancement and possible detachment of the outer sleeve 134 from the inner cylinder 162 as well as an inadvertent return of the outer sleeve 134 to the retracted position of FIG. 19. Therefore, a disposal cartridge is created (in FIG. 20) having the inner cylinder 162 and outer sleeve 134 locked in the axially extended position with the hypodermic needle 138 completely surrounded and shielded, so that the syringe 160 may be safely handled while avoiding an accidental needle strike and the possible spread of a contagious disease.

FIGS. 24-27 of the drawings show a sixth embodiment of the present invention for a cost-effective, efficiently manufactured, and relatively easily assembled shielded safety syringe. Like the previously described syringes, the syringe 180 of FIGS. 24-27 includes an inner cylinder 182 and an outer protective sleeve 184 which are to be coaxially aligned and axially extensible relative to one another from a retracted position (of FIG. 25) to an axially extended position (of FIG. 26). The inner cylinder 182 and outer sleeve 184 are preferably fabricated from a moldable, relatively flexible material, such as radiation grade polypropylene. The inner cylinder 182 has an open, flanged proximal end for receiving an evacuated phlebotomy tube (not shown) and a substantially closed distal end wall 185. A screw-threaded hub 186, which carries a double ended needle 188, is to be received within a distal bore formed through a neck 190 which extends from the distal end wall 185 of cylinder 182, whereby one end of needle 188 projects outwardly from the inner cylinder 182, and the opposite end of needle 188 projects into the interior of the inner cylinder for communication with the phlebotomy tube.

Coextensively formed with and projecting outwardly from the inner cylinder 182 is a pair of parallel aligned and ramp-shaped lips 192 and 192 which extend continuously and peripherally around the distal end of cylinder 182. The ramp-shaped lip 194 is spaced proximally from the ramp-shaped lip 192 such that a peripheral catch groove 196 is formed therebetween. The ramped lip 192 slopes upwardly in a proximally oriented direction, while the ramped lip 194 slopes upwardly in a distally oriented direction. Moreover, ramped lip 192 has a larger diameter (i.e. a greater elevation above inner cylinder 182) than does ramped lip 194.

Coextensively formed with and projecting outwardly from the proximal end of inner cylinder 192 is a ramped-shaped release catch 198. Extending around the open proximal end of inner cylinder 182 is a pair of oppositely disposed and radially projecting flange members 200. Release catch 182 is spaced distally from one of the flange members 200 so that a gap 202 is formed therebetween. A plurality of slots 204 are formed in the inner cylinder 182 and extended axially from the open proximal end thereof. Slots 204 maximize the flexibility of the inner cylinder 182 at the proximal end thereof when the opposing flange members 200 are rotated in a radially inward direction in a manner and for a purpose that will soon be described.

The outer sleeve 184 includes an open proximal end for receiving the inner cylinder 182 therethrough and a substantially closed distal end 208. An opening 210 is formed through distal end 208 for receiving one end of a double ended needle 188 when inner cylinder 182 and outer sleeve 184 are moved to the retracted position of FIG. 25. An annular rim 212 is coextensively formed with and extended inwardly around the periphery of the proximal end of outer sleeve 184. A plurality of slots 214 are formed in the outer sleeve 184 and extended axially from the open proximal end thereof to maximize the flexibility of the proximal end when outer sleeve 184 rides over the inner cylinder 182 between the axially extended and retracted positions, as will now be disclosed in detail.

Figure 25:
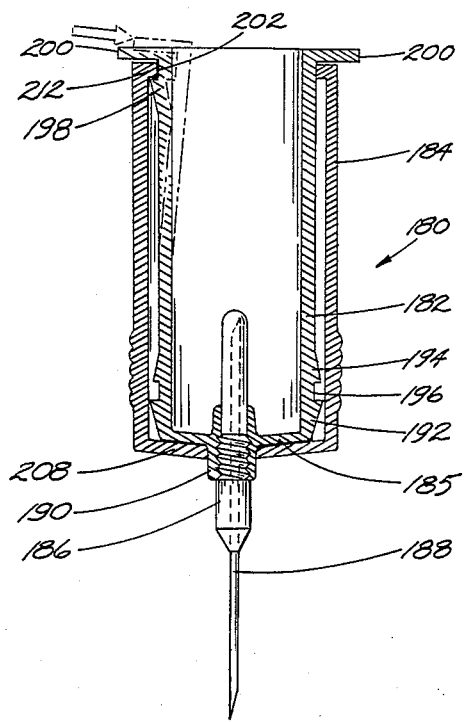
FIG. 25 shows a cross-section of the syringe of the sixth embodiment with the inner cylinder and outer sleeve locked in a retracted position relative to one another.
Figure 26:
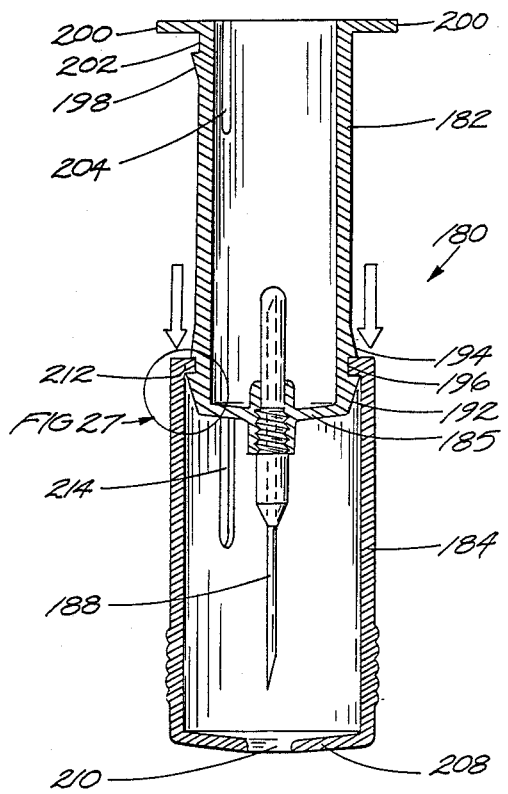
FIG. 26 shows a cross-section of the syringe of the sixth embodiment with the inner cylinder and outer sleeve axially advanced relative to one another to the extended position.

The operation of shielded safety syringe 180 is described while continuing to refer to FIGS. 24-27 of the drawings. Initially, the inner cylinder 182 and outer sleeve 184 are interconnected to one another to form the syringe assembly 180 by merely applying an axially directed force (in the direction of the reference arrow 216 of FIG. 24) against the closed distal end 208 of outer sleeve 184, whereby inner sleeve 182 is received through the open proximal end of sleeve 184. More particularly, the aforementioned axially directed force is sufficient to drive the annular rim 212 of outer sleeve 184 up the relatively large diameter, ramped lip 192 of inner cylinder 182, whereby to lift rim 212 up and over the top of catch groove 196 and down ramped lip 194 (best illustrated in FIG. 27). The annular rim 212 of outer sleeve 184 then rides axially and proximally along inner cylinder 182, up the ramped release catch 198, and into the gap 202 formed between release catch 198 and flange member 200. Outer sleeve 184 is correspondingly moved to and locked in the retracted position relative to inner cylinder 182, as is best shown in FIG. 25.

As a very important advantage of the presently described safety syringe embodiment, the inner cylinder 182 and outer sleeve 184 are interconnected to one another when an axially directed force is applied to outer sleeve 184 to cause the outer sleeve to ride over the inner cylinder until annular rim 212 is received within gap 202. That is to say, and as will be appreciated by those skilled in the art, the safety syringe 180 acts as its own assembly fixture and requires no external fixtures, jigs, chucks, or the like, which are otherwise used in the manufacture of conventional shielded syringes. Accordingly, the safety syringe 180 may be easily assembled and efficiently manufactured, inasmuch as cost inefficient, external handling and aligning equipment may be avoided.

The inner cylinder and outer sleeve of known shielded syringes have respective, distally extending, screw threaded necks which are aligned with one another and screwed together to lock the syringe assembly in a retracted position and thereby expose one end of a double ended needle. However, as another important advantage of the present safety syringe 180 and, more particularly, by virtue of the release catch 198, the conventional, distally aligned, screw-threaded necks of the inner cylinder and outer sleeve are eliminated, whereby to facilitate molding of the safety syringe. That is to say, and unlike known syringes, the inner cylinder 182 and outer sleeve 184 of the syringe 180 are automatically aligned with and interconnected to one another in the retracted position of FIG. 25 when the annular rim 212 is received within the gap 202 between release catch 198 and flange member 200, so as to avoid the heretofor required step of screwing the conventional inner cylinder and outer sleeve together at their respective screwthreaded necks.

With the safety syringe 180 in the retracted position of FIG. 25, one end of hypodermic needle 188 is exposed for making a single veni puncture through the skin of a patient, so that one or more evacuated blood collection phlebotomy tubes (not shown) may be successively interfaced with the opposite end of needle 188 so as to be infused with one or more samples of the patient's blood. After the last blood sample has been taken, and in order to avoid an accidental needle strike, the outer sleeve 184 is grasped and pulled to the axially extended position of FIG. 26, in a manner in which is now disclosed in detail.

More particularly, the health care worker uses a first hand to apply equal and opposite forces to the opposing flange members 200 of inner cylinder 182, whereby to cause the proximal end of the inner cylinder to rotate slightly in a radially inward direction (as illustrated in FIG. 25 in phantom). An inward rotation of the proximal end of inner cylinder 182 will correspondingly cause the release catch 198 and the adjacent gap 202 to be rotated out of engagement with annular rim 212. With the catch 198 and gap 202 in the rotated position, and the annular rim 212 released from engagement therewith, the health care worker uses his opposite hand to grasp the outer sleeve 184 and advance such sleever axially and distally relative to inner cylinder 182 and towards the axially extended position of FIG. 26. The axial advancement of outer sleeve 184 causes a corresponding axial advancement of the annular rim 212 thereof, such that rim 212 rides over the inner cylinder 182 and up the proximally oriented, ramped lip 194. The continued axial advancement of outer sleeve 184 relative to inner cylinder 182 will cause the annular rim 212 to be snapped into the catch groove 196 between ramped lips 192 and 194. A positive self-locking feature is thereby established, because the rim 212 of outer sleeve 184 is securely and permanently retained within groove 196 between the elevated lips 192 and 194. Hence, the lips 192 and 194 form stops to prevent both the continued axial advancement and possible detachment of the outer sleeve 184 from the inner cylinder 182 as well as an inadvertent return of the outer sleeve 184 to the retracted position of FIG. 25. Therefore, a disposal cartridge is created (in FIG. 26) having the inner cylinder 182 and outer sleeve 184 locked in the axially extended position with the needle 188 completely surrounded and shielded, so that the syringe 180 may be safely handled and discarded while avoiding an accidental needle strike and the possible spread of a life threatening contagious disease.

It will be apparent that while preferred embodiments of the present invention has been shown and described, various modifications and changes may be made without departing from the true spirit and scope of the invention.

Having thus set forth the preferred embodiments of this invention, what is claimed is:

1. A shielded syringe assembly comprising an inner syringe cylinder having an open proximal end and a substantially closed distal end, a hypodermic needle supported at and extending outwardly from said distal end, and an outer protective sleeve having an open proximal end and an opening in a substantially closed distal end, said outer sleeve coaxially aligned with and axially advanceable relative to said inner cylinder from a retracted position, where said needle projects outwardly through the opening in said sleeve, to an extended position, where said needle is located within and completely surrounded by said sleeve;

said outer sleeve having means projecting radially inward thereof;

said inner cylinder having first catch means located adjacent the proximal end thereof and second catch means located adjacent the distal end, each of said first and second catch means including at least one stop member projecting radially outward from said inner cylinder adjacent the proximal and distal ends thereof, respectively;

said first catch means releasably engaging the inwardly projecting means of said outer sleeve when said sleeve is located in the retracted position, such that said inwardly projecting means rides over and drops behind the at least one stop member of said first catch means to prevent the inadvertent relocation of said sleeve to the extended position, and said second catch means engaging the inwardly projecting means of said outer sleeve when said sleeve is axially advanced relative to said inner cylinder from the retracted to the extended position, such that said inwardly projecting means rides over and drops behind the at least one stop member of said second catch means to prevent the return of said sleeve to the retracted position.

2. The syringe recited in claim 1, wherein the radially inward projecting means of said outer sleeve is a rim which extends continuously around the proximal end of said sleeve.

3. The syringe recited in claim 1, wherein said first catch means includes a recess formed at the proximal end of said inner cylinder for receiving therewithin the inwardly projecting means of said outer sleeve.

4. The syringe recited in claim 3, wherein said first catch means includes a pair of axially spaced and radially outward extending stop members, said recess being located in the space between said pair of stop members.

5. The syringe recited in claim 1, wherein said at least one stop member of said first catch means is ramp-shaped to guide the inwardly projecting means of said outer sleeve over and behind said stop member when said outer sleeve is located in the retracted position.

6. The syringe recited in claim 1, wherein said second catch means includes a recess formed at the distal end of said inner cylinder for receiving therewithin the inwardly projecting means of said outer sleeve.

7. The syringe recited in claim 6, wherein said second catch means includes a pair of axially spaced and radially outward extending stop members, said recess being located in the space between said pair of stop members.

8. The syringe recited in claim 1, wherein the at least one stop member of said second catch means is ramp-shaped to guide the inwardly projecting means of said outer sleeve over and behind said stop member when said outer sleeve is advanced from the retracted to the extended position.

9. The syringe recited in claim 8, wherein said second catch means includes a second stop member that is also ramp-shaped, said second ramp-shaped stop member being spaced distally from said first ramp-shaped stop member and having a greater elevation relative to said inner cylinder than said first member.

10. The syringe recited in claim 1, wherein said second catch means comprises a pair of axially spaced, ramp-shaped lips which extend peripherally and continuously around the distal end of said inner cylinder, the inwardly projecting means of said outer sleeve being received in the space between said pair of lips.

11. A shielded syringe assembly comprising an inner syringe cylinder having an open proximal end and a substantially closed distal end, a hypodermic needle supported at and extending outwardly from said distal end, and an outer protective sleeve having an open proximal end and an opening in a substantially closed distal end, said outer sleeve coaxially aligned with and axially advanceable relative to said inner cylinder from a retracted position, where said needle projects outwardly through the opening in said sleeve, to an extended position, where said needle is located within and completely surrounded by said sleeve;
- said outer sleeve having means projecting radially inward thereof;
- said inner cylinder having first catch means located adjacent the proximal end thereof and second catch means located adjacent the distal end;
- said first catch means releasably engaging the inwardly projecting means of said outer sleeve adjacent the proximal end of said cylinder when said sleeve is axially advanced relative to said inner cylinder from the retracted to the extended position; and
- means by which to rotate the proximal end of said inner cylinder in a radially inward direction, to thereby move said first catch means out of engagement with the inwardly projecting means of said outer sleeve when said outer sleeve is located in the retracted position relative to said cylinder.

12. The syringe recited in claim 11, wherein said means by which to rotate include axially extending slots formed through a portion of said inner cylinder from the proximal end thereof.

13. The syringe recited in claim 12, wherein said means to rotate further includes at least one flange projecting radially outward from the proximal end of said inner cylinder.

14. A shielded blood collection device comprising:
- an inner cylinder having an open proximal end and a substantially closed distal end, and a double ended hypodermic needle supported at said distal end such that a first end of said needle extends outwardly from said cylinder and the second end extends inwardly for communicating with the interior of said cylinder;
- an outer protective sleeve having an open proximal end and an opening formed in a substantially closed distal end, said outer sleeve being coaxially aligned with and axially advanceable relative to said inner cylinder from a retracted position, where the first end of said needle projects through the distal opening in said sleeve for making a veni puncture, to an extended position, where the first end of said needle is located within and completely surrounded by said sleeve;
- one of said outer sleeve or said inner cylinder having retaining means projecting radially therefrom; and
- the other end of said outer sleeve or said inner cylinder having at least one raised stop member located adjacent each of the proximal and distal ends thereof,
- said outer sleeve being disposed to the retracted position such that said retaining means is engaged by a first of said at least one raised stop members to prevent the inadvertent relocation of said sleeve to the extended position, or said outer sleeve being disposed in the extended position such that said retaining means is engaged by the other of said at least one raised stop members to prevent the return of said sleeve to the retracted position.

15. The blood collection device recited in claim 14, wherein said at least one raised stop member located adjacent the proximal end of the other of said outer sleeve or inner cylinder is ramp-shaped.

16. The blood collection device recited in claim 14, wherein said at least one raised stop member located adjacent the distal end of the other of said outer sleeve or inner cylinder is ramp-shaped.

17. The blood collection device recited in claim 14, wherein a pair of axially spaced, raised stop members are located adjacent the proximal end of the other of said outer sleeve or inner cylinder for receiving said retaining means in the space therebetween.

18. The blood collection device recited in claim 14, wherein a pair of axially spaced, raised stop members are located adjacent the distal end of the other of said outer sleeve or inner cylinder for receiving said retaining means in the space therebetween.

19. The blood collection device recited in claim 14, wherein said radially projecting retaining means is a lip formed around the periphery of the one of said outer sleeve or said inner cylinder.

20. The blood collection device recited in claim 14, wherein each of said at least one raised stop members is ramp-shaped for guiding said retaining means over and behind said stop members when said outer sleeve is moved relative to said inner cylinder between the retracted and extended positions.

* * * * *